United States Patent [19]
Hecht

[11] Patent Number: 4,753,655
[45] Date of Patent: Jun. 28, 1988

[54] TREATING VISION

[76] Inventor: Sanford D. Hecht, 87 Levbert Rd., Newton Center, Mass. 02159

[21] Appl. No.: 18,858

[22] Filed: Feb. 24, 1987

Related U.S. Application Data

[63] Continuation of Ser. No. 601,380, Apr. 17, 1984, abandoned.

[51] Int. Cl.⁴ ............................................. A61F 2/16
[52] U.S. Cl. ................................................... 623/6
[58] Field of Search ............................................ 623/6

[56] References Cited

U.S. PATENT DOCUMENTS

| | | | |
|---|---|---|---|
| 4,074,368 | 2/1978 | Levy et al. | 623/6 |
| 4,327,450 | 5/1982 | Girard | 623/6 |
| 4,573,998 | 3/1986 | Muzzocco | 623/6 |
| 4,657,547 | 4/1987 | Maggi | 623/6 |

FOREIGN PATENT DOCUMENTS 0069089  1/1983  European Pat. Off. ............ 623/6

Primary Examiner—Richard J. Apley
Assistant Examiner—James Prizant
Attorney, Agent, or Firm—Charles Hieken

[57] ABSTRACT

An artificial lens is cantilevered from a support rod in the vitreous chamber of the eye with the other end of the support rod affixed to an anterior chamber lens, the support for it, the sclera or (natural) lens capsule. There may be a number of support rods and a number of lenses cantilevered from support rods in the vitreous cavity.

1 Claim, 4 Drawing Sheets

TREATING VISION

This application is a continuation of U.S. application Ser. No. 601,380, filed 4-17-84 now abandoned.

The present invention relates in general to improving and/or maintaining vision and more particularly concerns novel apparatus and techniques for improving vision with eye implants. The invention may be used with or without other natural or artificial lenses and arranged for adjustment to achieve particular optical effects.

An example of a prior art aphakic intraocular implant is disclosed in an article entitled "Pars Plana Pahcoprosthesis" (aphakic intraocular implant): A Preliminary Report by Louis J. Girard on page 19 of OPTHALMIC SURGERY for January 1981. Among other prior art are U.S. Pat. Nos. 2,834,023, 3,961,379, 3,992,563, 4,021,382, 4,028,082, 4,110,848, 4,122,556, 4,159,546, 4,205,518, 4,214,585, 4,242,760, 4,338,687, 4,340,979, 4,343,050 and 4,342,123.

It is an important object of this invention to provide methods and means for maintaining and/or improving vision with eye implants.

Numerous other features, objects and advantages of the invention all become apparent from the following specification when read in connection with the accompanying drawing in which.

Figure 1:
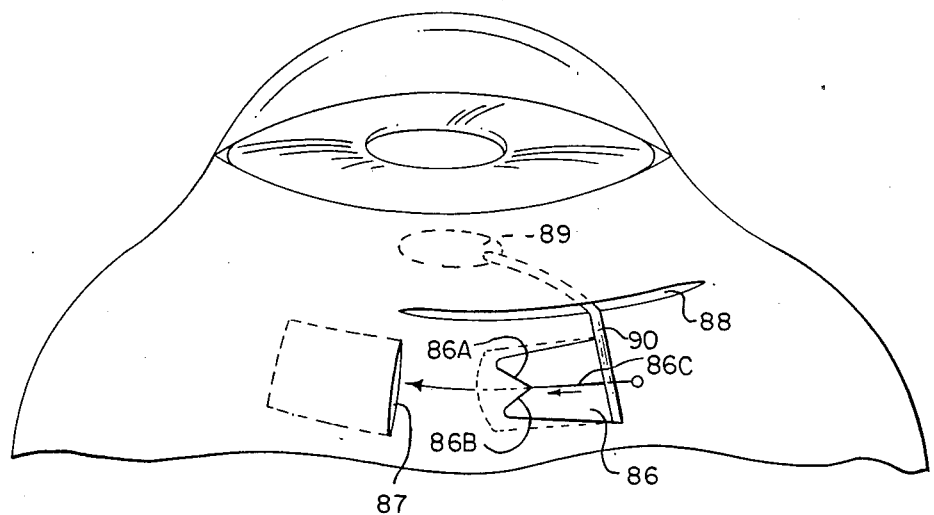
FIG. 1 illustrates a foot entering a pocket in the sclera.

FIG. 1 is a magnified view showing how a foot 86 may be inserted into an intrascleral pocket 87 with optic 89 and support rod or handle 90 passing through a full thickness wound 88 in the sclera into 89 the posterior chamber. Foot 86 may have parts 86A and 86B that enter pocket 87 collapsed and then uncollapse as control member 86C is pressed to seat the foot 86C firmly in pocket 87.

When fixed to sclera, the feet can have varied and sufficiently effective area to stabilize implants, or any other systems or parts requiring support and stability about the eye. The amount of feet, their placements, their sizes, shapes and configurations may be varied to accommodate differing sizes, configurations, and (mass) weights of systems or parts, and the foot size, configuration and thickness may be varied to produce scleral buckling effects so as to prevent retinal detachments or treat vitreous traction or retinal breaks or other retinal and vitreous pathology. The feet may be episcleral or intrascleral or endoscleral or combinations of these. They may have notches, grooves, irregularities or openings or combinations in the center or on edges to allow tissue (scleral or otherwise) to grow across, and/or be sutured to sclera, and/or they can be made of substances capable of cellular invasion by human cells and tissue, all of this improving their fixation. They can be fixed to sclera anywhere except where optic nerves enter or where sclera is too thin. The invention contemplates foot fixation at, adjacent to, or nearby the entry incision of an intraocular implant, as well as at a greater distance from it, as for example, on the opposite side of the globe. Feet with handles, cantilevers or rods (etc.) having jogs, notches or other variations along their lengths may be secondarily placed to modify or stabilize an implant system.

Scleral pockets (for intrascleral feet) not only enable a sealing of the eye using the eye's own natural wall, but also greatly increase the operative safety of intraocular implant insertion. Pockets provide future safety by firm fixation of implant systems. Intraoperatively a pocket may be partly closed or be fully open, having one or more lamellar scleral flaps to be closed over a foot. Flaps may be partly sutured before foot placement as well. A pocket may be open on one side only, thereby giving extra security to a foot and requiring less suturing (gluing). Pockets may be anywhere except where the optic nerve enters the eye or where the sclera is too thin. Pockets may be of many sizes and shapes. Thick or thin sclera may be reinforced by human and/or animal tissue to improve or enable foot fixation.

Entry full thickness incisions may be wholly or in part, at the limbus to anywhere on the sclera except where the optic nerve enters. The limbus is the area of the junction of sclera and cornea. Incision sites are varied depending on the patient's individual requirements. Transretinal implants enter the eye more posteriorly, where the eye muscles are further apart. This gives space for large feet and enables more footentry incision relationship possibilities without having to retract muscles. Full thickness incisions may be varied. For example, they may be stepped, slanting, or perpendicular to the coats of the eye. They may be any length and any pattern ("S"-type, straight, "Z"-type, "L"-type, "U"-type, curved, or other shapes or combinations). They may be within an intrascleral pocket, under the implant foot, in an episcleral foot fixation, or adjacent to the pocket or episcleral foot or distant from it, etc. They may share a common episcleral tissue (lamellar) flap or may have separate scleral flaps or none at all, depending on the individual eye's or surgeon's requirement. They may be closed with sutures, glue or any other suitable methods.

Many implant parts may be malleable to enable the surgeon to alter the implant position or foot, contours as needed. In addition, folded ribbon or coil or corrugated arrangements may be placed in cantilevers, arms and double (eye) wall supports to enable adjusting the position of implants or their parts by the surgeon. Adjustable rod and sleeve type and other extensions may also be used for this purpose.

Extensions (such as rod and sleeve type) may be used to (1) enable safer placement of implants so as to extend from within the eye only after they are securely fixed to the sclera)(globe); (2) to enable the patient to move a system in and out of use by head movements, magnetic substances, or other techniques and (3) to enable "play" or automatic adjustability of length in a double (eye) wall (transverse) support so as not to put unnatural stresses on the eye wall and foot fixation when the globe is compressed, pulled or pushed upon. Spring and/or elastic arrangements may also be used alone or in combination with the rod-sleeve type extensions for this purpose.

Figure 2:
FIG. 2 shows an extensible lens support.

FIG. 2 shows an extensible support comprising a sleeve 91 supported from a malleable portion 92 and foot 92A and carrying an extensible rod 93 supporting optic 94. Rod 93 may carry a number of axially spaced elevations, such as 95, for engaging the lip of sleeve 91 and allowing the surgeon to position extensible arm 93 at a desired position.

Preoperative marking of the eye to indicate its vertical and horizontal meridians, or other features, is often necessary as well as preoperative measurement of pupil size and position. Furthermore, saccade and other eye movement studies as well as the range of motion of the patient's neck (and spine) may be needed. These studies are necessary when placing some movable implant systems. Preoperative ultrasound measurements of scleral thickness and infrared blood vessel imaging may be required.

Simultaneous filtering sclerectomy or sclerotomy may be created as needed to lower the intraocular pressure and allow the implant entry wound and the scleral pocket or episcleral site to correctly heal.

Figure 3A:
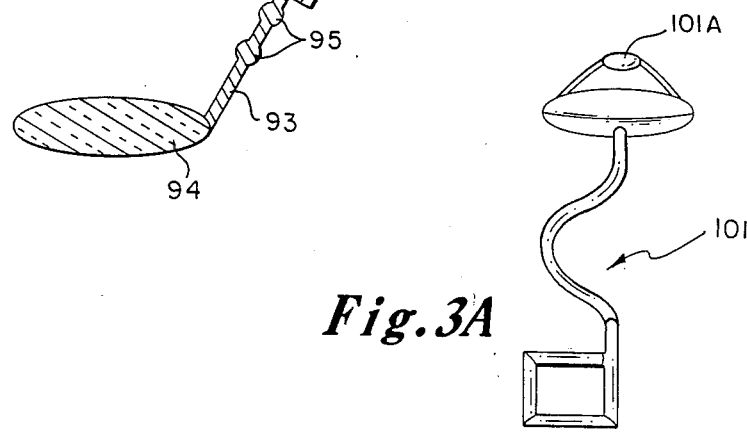
FIGS. 3A and 3B show plan and side views, respectively, of the cantilevered lens assembly for attachment in the pocket as shown in FIG. 1.
Figure 3B:
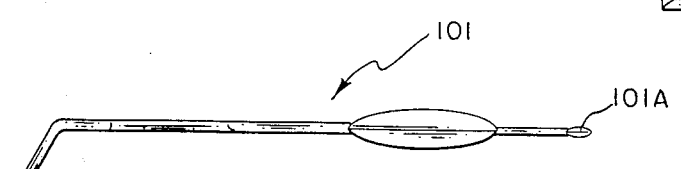

The following is one of many possible surgical approaches to vitreous cavity implants and posterior chamber implants which are intrascleral foot fixed. Preoperative studies and marking are recommended for most movable implants. Such studies may be of use in nonmovable systems as well. FIGS. 3A and 3B are perspective and edge views, respectively, of an assembly 101 with a nonmoveable float 101A, an optic, jog and foot for implanting according to the invention.

Figure 4:
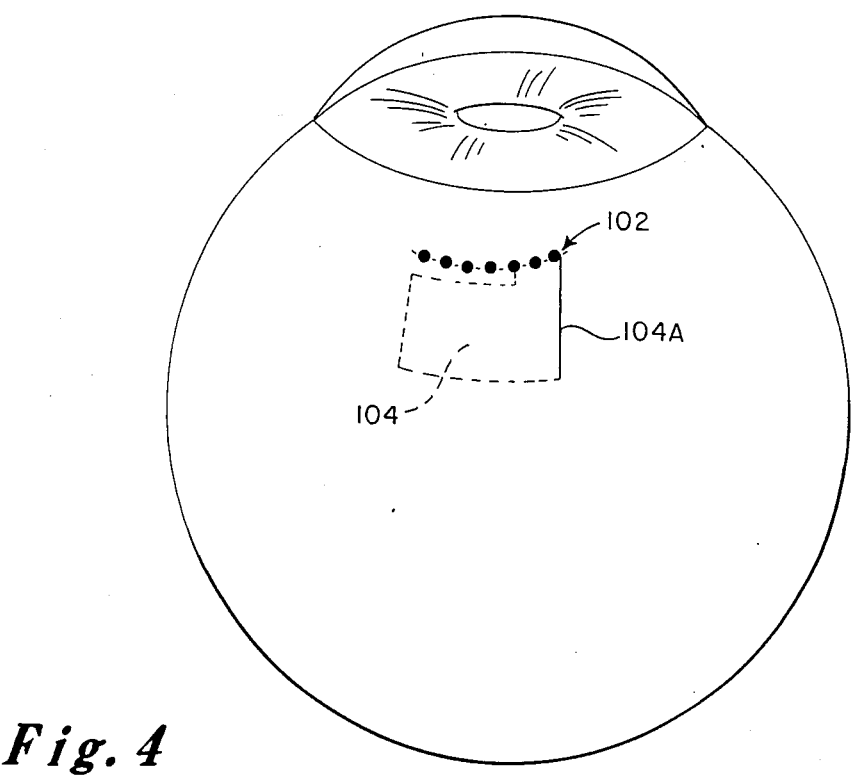
FIGS. 4-9 show steps in an implant procedure according to the invention.
Figure 5:
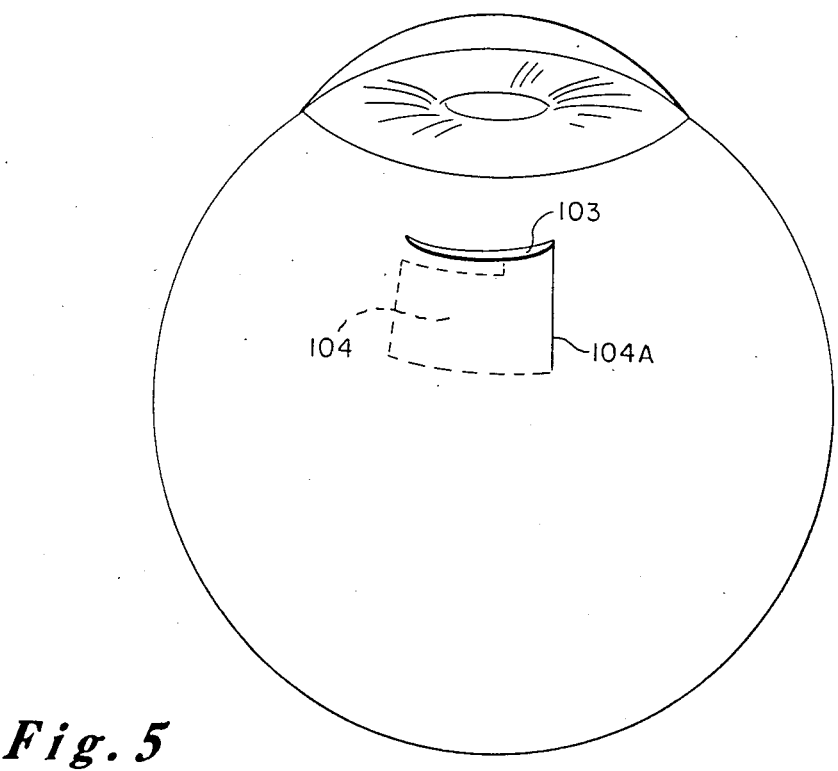

The conjunctiva and Tenon's capsule are incised and tracted away. Cautery is applied as required. The measurements of the distance from the limbus (corneal-scleral junction) to the intended full thickness eye incision (for implant entry) is made using calipers. The relationships of the intended incision site to the vertical and horizontal (premarked ocular (globe) meridians is noted and may be measured with a small sterile protractor. For each scleral foot supported implant style there are recommended distances between globe entry incisions, scleral foot fixation placements, and globe meridians. If a pocket is to be made, it is placed accordingly. Incision-pocket-globe meridian orientation and marking devices may be provided for the surgeon's use. The correct intended dried incision site 102 is marked with a thin-tipped sterile dye marker as shown in FIG. 4. An intrascleral pocket 104 with one end open 104A may be created with a knife and/or blunt or semi-sharp instruments adjacent to the intended full thickness implant (intraocular) incision 102 as shown in FIG. 4. The correctness of the pocket size is tested with a "test foot" instrument of the same size and shape as the foot (feet) of the implant to be used. The human lens may have been previously removed. If not, it may be then removed by any method desired, and the implant incision is made by entering at the premarked (incision) site 103 FIG. 5. Vitreous may be removed or not. Healon ® (sodium hyaluronate), and/or other substances, may be used to move vitreous away or, if the vitreous is removed, air, Healon ®, or substances of the same or similar function may replace it during surgery. There may be liquid, air or other inflow, into the globe from the same or another entry site or sites.

Figure 6:
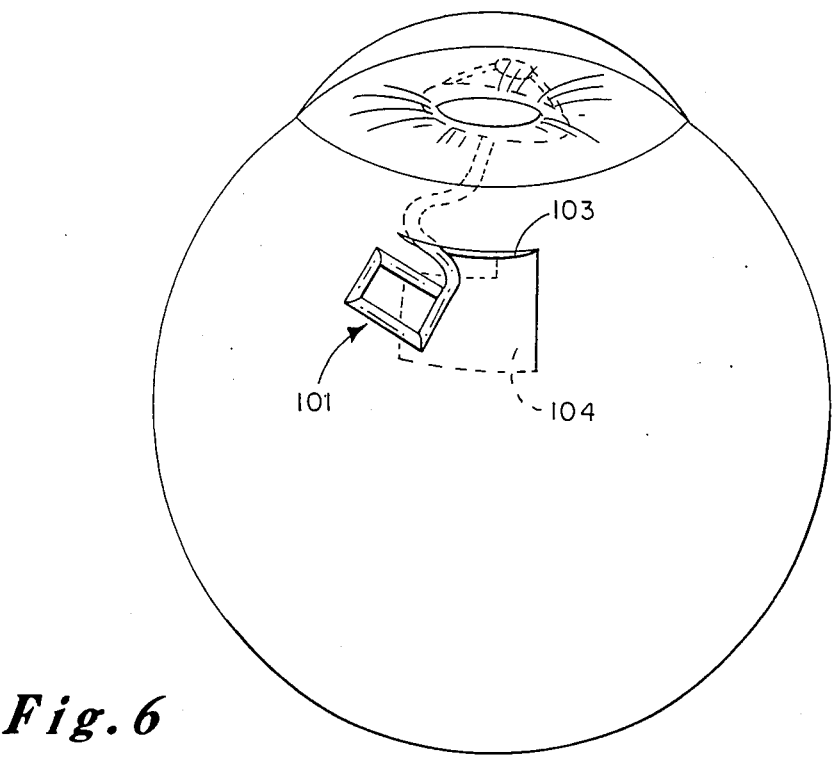
Figure 7:
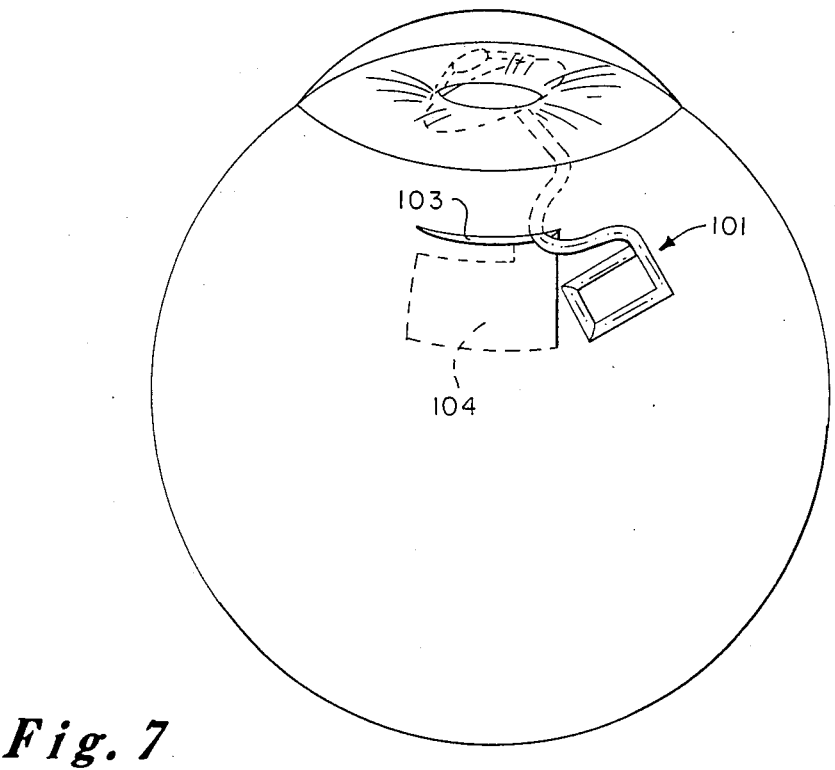

The implant 101 is placed through the full thickness incision 103 into the eye and its foot is placed into the scleral pocket 104 as shown in FIGS. 6 and 7. It is here that the value of the large jog or bend in the cantilever (or jog bend such as this in any intraocular support) becomes apparent because it more easily and safely enables a secure foot into scleral pocket placement at a potentially dangerous time. Depending on the implant required (and therefore the scleral pocket-entry incision relationship) the jog may be made in many directions. In summary when the implant enters the eye, the large jog or bend enables the surgeon to more safely shift the foot (and implant) to a position where the foot can be placed into an open or partly open scleral pocket.

Figure 8:
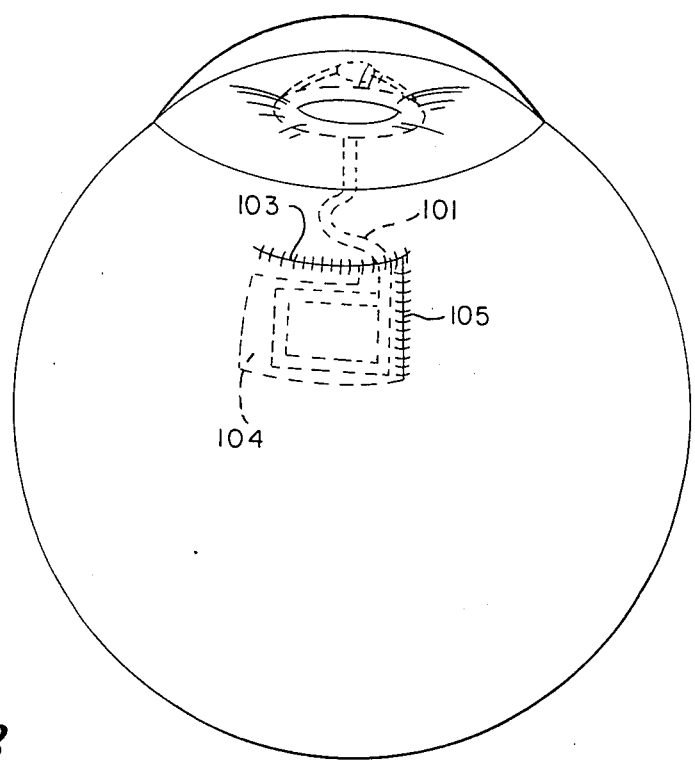
Figure 9:
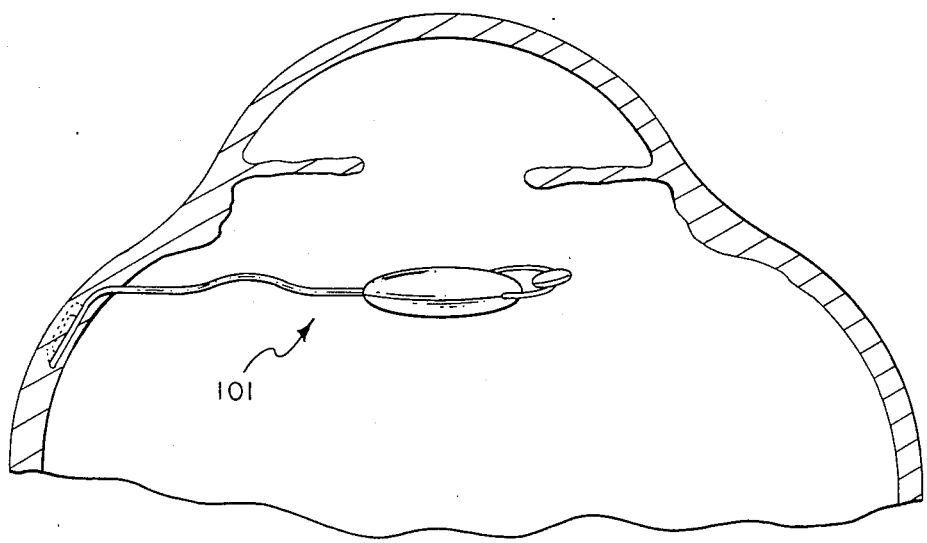

Some implants may have a "handle" where they can be safely and easily grasped with existing instruments or those designed specifically for the purpose. The entry wound is usually closed with permanent sutures 105 as shown in FIG. 8. The entry lamellar scleral flap which was raised to create the pocket was originally extended to the entry incision. It is also closed with permanent type sutures. The overlying conjunctiva and Tenon's capsule which were incised and moved out of the way are sutured back to their original positions. The globe intraocular tension tenses the sclera and now enables (intraoperative) adjustment of the implant if needed, using small intraocular instruments while viewing the implant through the pupil (FIG. 9).

Glycerin may be used to dehydrate the sclera so that the surgeon can see the depth of the knife or instrument while making the pocket but some surgeons may prefer to thicken the sclera with sterile water or hypotonic solutions instead.

Drug or Chemical Delivery Implant Systems may have roles in the therapy of uveitis, endophthalmitis, neoplasms, infectious diseases, metabolic, degenerative, genetic and other disorders (e.g. diabetes, retinitis pigmentosa, and other disorders). The methods may include:

1. Conduit or channel methods (a hollow or grooved implant part or parts which allow drug flow into and/or out of the eye) and separate infusion and aspiration passages may be provided;
2. conduit or channel methods combined with valves and/or differentially permeable parts or membranes;
3. depot methods with the replaceable (or not) depot or depots of drugs or chemicals connected to implant support structures or any parts of implants;
4. perforating, self-sealing methods—needles for injection of substances penetrate self-sealing membranes or barriers; and
5. combinations of the above four.

Implants may also be a source of electrical energy in or on or near the eye so as to facilitate or limit drug penetration and/or produce other biologic effects. Drug or chemical delivering extraocular implants may function alone, without associated intraocular drug or chemical delivery, or other implants.

Barriers or membranes which are differentially permeable, may be used with both depot and conduit systems. Drug or chemical delivery depots may be within the eye, attached to or within implant parts, or may be connected to episcleral, intrascleral, orbital or periorbital implants.

Depots are implant parts which may be permanently connected to implants or may be removable. They contain drugs or chemicals, the release of which may be controlled by valves or other means. Such depots may be resuppliable with drugs or chemicals. They may be combined with optical or intraocular pressure controlling implants or both.

Barriers or membranes selectively permeable to some chemicals but not to most or all bacteria or viruses may be used with both depot and conduit systems. Depots may be within the eye, attached to or inside implant parts, or may be episcleral, intrascleral, orbital, or periorbital.

The implants may alter intraocular pressure. Outflow of intraocular fluids may be controlled by conduits or channels of various sizes which may have adjustable valves or other impediments to control the outflow rate of aqueous humor. Such implants may be used as collectors of intraocular substances, as may some drug and chemical delivery implants.

Photo cells, photovoltaic cells, or any devices that convert electromagnetic energy to galvanic or other current, rechargeable or nonrechargeable batteries for producing and/or storing electricity, electromagnetic radiation detection devices, electronic circuitry, e.g. radio circuits and circuits enabling pre-programming and/or programming and/or controlling of implant activity or combinations of these may be implanted intra- or extraocularly or both. Programming may also be used in external radios or ultrasound transmitters and receivers which may be used in combination with the implants.

Using any or all of these methods the devices may be fixated by connection to intraocular sclerally and/or limbally and/or corneally fixed implant parts as well as extraocularly orbitally and periorbitally fixed implant parts or combinations of all these so as to provide therapy introcularly, orbitally, periorbitally or a combination of these. Orbital implants may be fixed episclerally as well.

Any support, such as a cantilever or transglobal support, may carry multiple implants, movable and/or stationary, such as optics.

There has been described novel apparatus and techniques for improving vision with eye implants. It is evident that those skilled in the art may now make numerous used and modifications of and departures from the specific embodiments described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. A method of positioning an intraocular implant comprising an element carried by a support rod at one end and having a foot at the other which method includes the steps of, making an incision in the sclera wall that passes through the sclera and is long enough to pass therethrough said element, said sclera wall having an external surface and an inner surface, forming a pocket in said external surface of said sclera near said incision, passing said element and a portion of said support rod through said incision that passes through said sclera wall, seating said foot in said pocket in said external surface, and closing said pocket with said foot seated therein and said incision.

* * * * *